(12) United States Patent
Levy

(10) Patent No.: US 6,191,293 B1
(45) Date of Patent: *Feb. 20, 2001

(54) TRANS-XANTHOPHYLL ESTER CONCENTRATES OF ENHANCED PURITY AND METHODS OF MAKING SAME

(75) Inventor: Luis W. Levy, Quito (EC)

(73) Assignee: Inexa, Industria Extractora C.A., Quito (EC)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 40 days.

(21) Appl. No.: 09/229,041

(22) Filed: Jan. 12, 1999

Related U.S. Application Data

(60) Provisional application No. 60/082,293, filed on Apr. 20, 1998, and provisional application No. 60/085,804, filed on May 18, 1998.

(51) Int. Cl.$^7$ ....................................................... C07C 1/00
(52) U.S. Cl. ........................... 554/12; 568/816; 568/834
(58) Field of Search .................................. 568/816, 834; 554/12

(56) References Cited

U.S. PATENT DOCUMENTS

| | | |
|---|---|---|
| 3,258,467 | 6/1966 | Anderson et al. . |
| 3,333,962 | 8/1967 | Prebluda et al. . |
| 3,523,138 | 8/1970 | Grant . |
| 3,539,686 | 11/1970 | Rosenberg . |
| 3,879,424 | 4/1975 | Surmatis et al. . |
| 3,989,757 | 11/1976 | Surmatis . |
| 3,997,679 | 12/1976 | Salkin . |
| 4,048,203 * | 9/1977 | Philip ................................ 260/412.8 |
| 4,105,855 | 8/1978 | Schulz et al. . |
| 5,382,714 | 1/1995 | Khachik . |
| 5,523,494 | 6/1996 | Torres-Cardona et al. . |
| 5,536,504 | 7/1996 | Eugster et al. . |
| 5,602,286 | 2/1997 | Muralidhara . |
| 5,648,564 | 7/1997 | Ausich et al. . |
| 5,747,544 | 5/1998 | Garnett et al. . |
| 5,876,782 | 3/1999 | Sas et al. . |

FOREIGN PATENT DOCUMENTS

| | | |
|---|---|---|
| 25 05 869 A1 | 8/1976 | (DE) . |
| 0 672 655 A1 | 9/1995 | (EP) . |
| 2 301 775 | 12/1996 | (GB) . |
| 08-048895 | 2/1996 | (JP) . |
| WO 96/40092 | 12/1996 | (WO) . |
| WO 97/23436 | 7/1997 | (WO) . |
| WO 98/45241 | 10/1998 | (WO) . |
| WO 99/20587 | 4/1999 | (WO) . |

OTHER PUBLICATIONS

John T. Landrum et al. "The Macular Pigment: A Possible Role In Protection From Age–Related Macular Degeneration," Advances in Pharmacology, vol. 38, pp. 537, 544 (1997).

* cited by examiner

*Primary Examiner*—Deborah D. Carr
(74) *Attorney, Agent, or Firm*—Akin, Gump, Strauss, Hauer & Feld, L.L.P.

(57) ABSTRACT

Trans-xanthophyll ester concentrates having a trans-xanthophyll ester content of at least four times greater and preferably at least nine times greater than the cis-xanthophyll ester content are obtained. Xanthophyll ester concentrates having a total xanthophyll ester content of at least 40 wt. % and preferably greater than about 55 wt. % are also obtained. A method of obtaining a trans-xanthophyll ester concentrate of high purity includes contacting plant material containing xanthophyll esters with a hydrocarbon solvent for a time sufficient to extract xanthophyll esters from the plant material, separating the hydrocarbon solvent and extract dissolved therein from the remaining plant material, evaporating the hydrocarbon solvent from the dissolved extract to obtain a crude xanthophyll ester concentrate, admixing the crude xanthophyll ester concentrate with an alcohol at approximately ambient temperature to dissolve non-xanthophyll impurities and cis-xanthophyll esters from the concentrate and removing the alcohol containing impurities and cis-xanthophyll esters from the crude trans-xanthophyll concentrate to obtain a purified trans-xanthophyll ester concentrate. By using only the corollas of marigold flowers, lutein ester concentrates of high purity are obtained with pesticide residues absent from the concentrate at parts per billion detection levels.

23 Claims, No Drawings

TRANS-XANTHOPHYLL ESTER CONCENTRATES OF ENHANCED PURITY AND METHODS OF MAKING SAME

CROSS REFERENCE TO RELATED APPLICATIONS

This application is based on U.S. provisional patent application Ser. No. 60/082,293, filed Apr. 20, 1998 and Ser. No. 60/085,804, filed May 18, 1998, the disclosures of which are incorporated herein by reference.

BACKGROUND OF THE INVENTION

Xanthophyll esters belong to the group of natural compounds known as carotenoids and are widely distributed in nature. They are fatty acid esters (e.g., palmitate and myristate esters) of such carotenoids as lutein and zeaxanthin. Zeaxanthin ester is the pigment contained in berries such as those of genus Lycium and Physalis. Lutein ester is the pigment that gives the yellow/red color to fruits such as oranges, peaches, papayas, prunes, and mangos. Lutein esters are also present in many flowers, particularly marigold flowers of genus Tagetes. Xanthophyll esters are generally found in nature as the trans-xanthophyll geometric isomer.

The marigold flower is the richest source of trans-lutein ester found in nature. Dried and ground marigold flowers have been used commercially since 1966 as botanical ingredients in animal feeds, and since 1969 as starting materials for the production of marigold extracts, which contain xanthophyll esters as the commercially important component, see e.g., Lackey, German Patent No. 1,224,597; Levy et al., Ecuadorean Patent No. 44. Marigold extracts are products of international commerce. They are used as pigmenting agents in animal feed formulations and as food coloring agents such as the European natural color E161b/lutein, see e.g., Levy et al., Ecuadorean Patent No. 44; Rosenberg, U.S. Pat. No. 3,539,686; Official Journal of the European Communities No. L-226/37.

Recent scientific research has shown that marigold extracts may be used as human nutritional supplements, based on important biological functions of lutein in humans such as prevention of cancer and prevention of a condition known as age-related degeneration of the macula of the human eye, among other possible uses of lutein esters in nutrition and medicine, see e.g. Chew et al., *Anticancer Research*, 16:3689 (1996); Marchand et al., "An Ecological Study of Diet and Lung Cancer in the South Pacific," *International Journal of Cancer*, 63:18–23 (1995); Park et al., "The Effect of Dietary Lutein on Growth of Mammary tumor in BALB/c Mice," *The FASEB Journal*, 11:2586 (1997); H. P. Kim et al., "Hepatoprotective Action of Zeaxanthin Palmitate from *Lycium chinense*," *Research Communications Molecular Pathology and Pharmacology*, 97:301–314 (1997); Landrum et al., *Experimental Eye Research*, 65:1:57 (1997). To be suitable for these important new applications in humans, marigold extracts must satisfy more stringent quality requirements than were necessary in the past.

For use in human nutritional supplements, xanthophyll ester concentrates must be essentially free of pesticide contamination. They should contain the xanthophyll ester in sufficiently high concentration, e.g., at least 40 wt. %, to allow for formulation into capsules and tablets, although lower concentrations may still be satisfactory for use as a nutritional supplement. To achieve the maximum possible bioavailability for xanthophyll-containing nutritional supplements, the xanthophylls should be present in their naturally-occurring ester form, not in saponified (i.e., free alcohol or diol) form, and the naturally-occurring trans-xanthophyll isomer should predominate, see e.g., Herbst et al., *FASEB J. Abstract* 11:2587 (1997); Johnson et al., *J. Nutrition* 127:1993 (1997).

Unfortunately, known commercial marigold extracts fail to meet one or more of these quality criteria. The largest producers of marigold extracts (companies in Peru, Mexico and Ecuador) produce extracts containing between 14 and 20 wt. % lutein ester, mainly for animal feed formulations. Inexa, Industria Extractora C.A. of Quito, Ecuador, also produces a superior grade containing about 35 wt. % lutein ester as a food color. Typically, these products have a large presence of non-xanthophyll lipids which are extracted from the plant material with the xanthophylls when standard extraction techniques are employed. Moreover, commercial lutein ester concentrates also usually contain about 20 to 30 wt. % of the total lutein ester in the cis-isomeric form, again due to standard conditions of industrial processing.

Finally, known lutein ester concentrates often contain residues of pesticides, which are introduced into xanthophyll-containing plant matter through common cultivation techniques, such as those used on marigold plantations, and are extracted along with xanthophyll esters by standard extraction processes. All of this makes the currently available commercial lutein ester concentrates unsuitable for use as human nutritional supplements.

Several different methods have been proposed in order to overcome these disadvantages. U.S. Pat. No. 4,048,203 of Philip describes the extraction of lutein esters from plant material, and further purification of the esters using alcohol at 75° C. However, this heat treatment results in an undesirably large proportion of the less-bioavailable cis-xanthophyll isomer in the final product. See Comparative Example 1 below.

U.S. Pat. No. 5,382,714 of Khachik describes a process for the isolation, purification, and recrystallization of lutein from saponified marigold oleoresin, and U.S. Pat. No. 5,648,564 of Ausich et al. describes a process for the extraction, isolation, and purification of comestible xanthophyll crystals from plants. However, neither of these processes produces xanthophylls in their natural, most bioavailable, ester form because they both require a saponification step, whereby the natural xanthophyll ester form present in the plant material is destroyed.

U.S. Pat. No. 4,105,855 of Schulz teaches a method for synthesizing symmetrical carotenoids, which may be esters in all-trans isomeric form. However, lutein is not a symmetrical carotenoid, and while zeaxanthin is symmetrical, the only ester of zeaxanthin mentioned by Schulz is the diacetate as a last intermediate step in obtaining the diol. Schulz does not teach the synthesis or extraction of xanthophyll palmitate and myristate esters or their concentrates.

Thus, it is evident that there is a need in the art for a method of producing, through extraction and purification of plant material, xanthophyll concentrates that have enhanced purity and contain predominantly trans-xanthophylls in their natural ester form.

BRIEF SUMMARY OF THE INVENTION

According to the present invention, trans-xanthophyll ester concentrates are obtained in which the trans-xanthophyll ester content of the concentrate is at least 4 times greater, preferably at least about 9 times greater, than the cis-xanthophyll ester content of the concentrate. The total concentration of the trans- and cis-xanthophyll esters is at least about 40% by weight of the concentrate, and pesticide residues are substantially absent from the concentrate at parts per billion detection levels. Preferred esters are those of the xanthophylls lutein and zeaxanthin. Additionally, the trans-xanthophyll ester concentrates of the invention may have a total xanthophyll ester content of greater than about 55% by weight of the concentrate and often 70 wt. % or more.

The present invention also includes a method of obtaining a trans-xanthophyll ester concentrate of high purity, comprising contacting plant material containing xanthophyll esters with a hydrocarbon solvent for a time sufficient to extract xanthophyll esters from the plant material, separating the hydrocarbon solvent and extract dissolved therein from the remaining plant material, evaporating the hydrocarbon solvent from the dissolved extract to obtain a crude xanthophyll ester concentrate, admixing the crude xanthophyll ester concentrate with an alcohol at approximately ambient temperature to dissolve non-xanthophyll impurities and cis-xanthophyll esters from the concentrate, and removing the alcohol containing impurities and cis-xanthophyll esters from the crude trans-xanthophyll concentrate to obtain a purified trans-xanthophyll ester concentrate.

The invention further includes a method of obtaining a trans-lutein ester concentrate of high purity, comprising removing all non-corolla flower parts from marigold flowers, contacting the marigold corollas with a hydrocarbon solvent for a time sufficient to extract lutein esters from the corollas, separating the hydrocarbon solvent and extract dissolved therein from the remaining corollas, evaporating the hydrocarbon solvent from the dissolved extract to obtain a crude lutein ester concentrate, admixing the crude lutein ester concentrate with an alcohol at approximately ambient temperature to dissolve non-xanthophyll impurities and cis-lutein esters from the concentrate, and removing the alcohol containing impurities and cis-lutein esters from the crude trans-lutein concentrate to obtain a purified trans-lutein ester concentrate.

DETAILED DESCRIPTION OF THE INVENTION

According to the present invention, plant material containing xanthophyll esters is dehydrated, milled, and extracted with an appropriate aliphatic hydrocarbon solvent. The solvent is removed, resulting in a solvent-free extract containing xanthophyll esters, referred to in the art as an oleoresin. In the present invention, the oleoresin so formed, which generally has a trans:cis-xanthophyll isomer ratio of 75:25 is stirred with an alcohol at ambient temperature, in order to remove non-xanthophyll impurities and fractionate the cis- and trans-xanthophyll isomers. The liquid fraction of the suspension containing impurities and the cis-xanthophyll isomer is then removed, leaving behind the solid fraction: a purified trans-xanthophyll ester concentrate having high purity, a xanthophyll ester content of at least 40 wt. %, and a trans:cis-xanthophyll isomer ratio of at least 4:1, and preferably at least 9.1.

Starting materials for the present invention may include any xanthophyll ester-containing plant materials. Marigold flowers, especially the corollas, are a preferred starting material for lutein ester concentrates, and berries of genus Lycium and Physalis are especially preferred starting materials for zeaxanthin ester concentrates. Other preferred starting materials for lutein ester concentrates include fruits like oranges, peaches, papayas, prunes, and mangos.

A preferred embodiment of the present invention involves production of lutein ester concentrates from the corollas of marigold flowers. At the time of harvest only fully developed marigold flowers are chosen, and the corollas are carefully separated from the other flower parts. Separation may be by hand or by machine, but separation by hand is preferred due to the delicate nature of the flowers and the difficulties of automation. Microscopic examination of the corolla fraction of the harvest should show that it is essentially free of sepals, calyxes, and especially ripe or unripe seeds. These non-corolla flower parts, especially the seeds, tend to have higher pesticide concentrations than the corollas, such that removal of the non-corolla flower parts after harvesting functions as a pre-extraction purification step in the present invention. This additional purification step allows for the production of lutein ester concentrates of enhanced purity, which have no detectable pesticide residues, such that they may be used in human nutritional supplements.

In the method of the present invention, the xanthophyll ester-containing plant matter is dehydrated and milled Fresh plant matter usually contains 80% of moisture. Dehydration is generally carried out by means of passing forced hot air through the plant matter until the moisture has been reduced to about 10%, using commercially available stationery tray dryers or rotary dryers. Milling of the dehydrated plant material is usually done in commercial hammer-mills fitted with a screen that assures the degree of fineness which allows good extraction of the xanthophyll ester, but not so fine as would prevent fast and adequate drainage of the extraction solvent. The plant matter is then mixed with an aliphatic hydrocarbon solvent to extract xanthophyll esters.

According to current practices in the art, hexane is the preferred aliphatic hydrocarbon solvent for xanthophyll ester extraction, because it has good selectivity and its boiling point allows for full removal of solvent residues from the resulting extract. Other preferred aliphatic hydrocarbon extraction solvents include pentane, heptane, and mixtures of these with hexane.

Extraction using hexane or another hydrocarbon solvent is performed according to procedures known in the art. In the laboratory, one kg of plant material is preferably percolated with six liters of hexane at ambient temperature over at least four hours. For industrial scale production of xanthophyll ester concentrates, a standard countercurrent hexane extraction plant is preferably used, such that one batch of 2,000 kg of botanical raw material is fully extracted with 12,000 liters of solvent at ambient temperature and discharged from the equipment every two hours.

Following extraction, the hydrocarbon solvent containing extracted xanthophyll esters is removed from the remaining plant material. Such removal is preferably accomplished by filtration through filter cloth. The hydrocarbon solvent is then evaporated from the xanthophyll esters dissolved therein, leaving a solvent-free extract, or oleoresin. The evaporation is preferably performed at low temperature, most preferably at a temperature between 40° C. and 50° C., under a reduced pressure of about 3 mm Hg. The resulting oleoresin generally has a trans:cis-xanthophyll isomer ratio of 75:25, as determined by HPLC peak heights.

The oleoresin is mixed with an alcohol at about ambient temperature to dissolve non-xanthophyll impurities and fractionate the cis- and trans-xanthophyll isomers. The time needed for purification and fractionation depends on the characteristics of the oleoresin with higher impurity levels requiring longer times. Mixing is preferably continued for between one and six hours, most preferably for about 3 hours. The progress of purification of the oleoresin may be monitored by taking periodic samples from the reaction mixture, separating the solid by filtration and analytically determining the ester and trans-isomer content of the separated solid sample, in order to assure that mixing is concluded promptly once the desired degree of purification has been achieved.

Fractionation of the cis- and trans-xanthophyll isomers into the liquid and solid fractions, respectively, of the oleoresin suspension is believed to occur because the cis-xanthophyll isomer is quite soluble in the ambient temperature alcohol, while substantial dissolution of the trans-xanthophyll isomer does not occur in the alcohol in this temperature range. Thus, in order to achieve the desired fractionation of cis- and trans-xanthophyll isomers, mixing is performed at about ambient temperature. Temperatures high enough to allow substantial dissolution of the trans-xanthophyll isomer or conversion of the trans- to the cis-xanthophyll isomer should be avoided. Preferably the temperature for the alcohol mixing step should not exceed 25° C., and most preferably a temperature between about 18° C. and about 22° C. should be used.

After the oleoresin has been mixed with alcohol at about ambient temperature, the solid fraction of the oleoresin/alcohol suspension, which will become a purified trans-xanthophyll ester concentrate after desolventization, has at least a 4:1, and preferably at least a 9:1, trans:cis-xanthophyll isomer ratio as determined by HPLC peak heights, although the original oleoresin had about the usual equilibrium trans:cis-xanthophyll isomer ratio of 75:25. Most xanthophyll ester concentrates of the prior art, which are purified by mixing with an alcohol hot enough to dissolve both xanthophyll isomers, also have about a 75:25 trans:cis-isomer ratio. The increased trans:cis-isomer ratio achieved by the methods of the present invention is desirable for xanthophyll ester concentrates that are to be used in nutritional supplements, because the trans-xanthophyll isomer is the naturally-occurring isomer and is believed to be more bioavailable than the cis-isomer.

The alcohol selected for use with the present invention must have a low enough boiling point that it may be fully removed from the final product at temperatures low enough to avoid conversion of the trans- to the cis-xanthophyll isomer, which is believed to occur gradually with increasing temperature. Preferred alcohols for use with the present invention include the lower (e.g., $C_1$–$C_6$) alkanols.

The solubility of non-xanthophyll impurities, as well as the solubilities of both the cis- and trans-xanthophyll isomers, increases with increasing molecular weight of the alcohol solvent. Thus, use of alcohols with higher molecular weights results in trans-xanthophyll ester concentrates of greater purity but lower yield, since more trans-xanthophyll esters are lost through dissolution into the liquid fraction of the alcohol/oleoresin suspension. Therefore, an alcohol of intermediate molecular weight should be chosen in order to balance the opposing trends of increasing purity and decreasing yield with increasing molecular weight of the alcohol. Thus, among the preferred lower alkanols, isopropanol is the most preferable because its intermediate molecular weight allows it to achieve good purification as well as good yield of the trans-xanthophyll ester concentrate.

A sufficient quantity of alcohol should be used to wash out most of the non-xanthophyll ester components and to fractionate the cis-/trans-xanthophyll isomers. The quantity of alcohol needed depends upon the characteristics of the oleoresin, which may be affected by variation in factors such as climate (e.g., amount of rainfall and amount of sunshine during growth and harvest of the xanthophyll ester-containing plant material), conditions of post-harvest dehydration, extraction temperature, etc. In general, the quantity of alcohol used for the alcohol mixing step of the present invention may be varied based on laboratory data, i.e., content of ester and cis-isomer, obtained before and during the mixing of the oleoresin with alcohol. The progress of the purification of the oleoresin is monitored throughout the alcohol mixing step, such that the volume of alcohol used, like the length of time taken for mixing, may be adjusted to achieve the highest possible purity at the lowest possible processing cost. Preferably between two and five parts alcohol by volume per each one part by volume of oleoresin are employed for the alcohol mixing step. However, a much greater excess of alcohol may be used in accordance with the present invention.

Once the desired degree of purity and isomer fractionation has been achieved through the alcohol mixing step, the solid fraction of the alcohol/oleoresin suspension is separated from the mixture, preferably by filtration or centrifugation. The solid fraction is further desolventized in a vacuum tray dryer, in order to obtain a purified trans-xanthophyll ester concentrate.

The purified trans-xanthophyll ester concentrate may then be melted at a temperature not exceeding 50° C. under an inert atmosphere, preferably of nitrogen gas, and poured into molds of any shape desired, preferably bar molds. After cooling until it reaches a solid condition, usually at about 20° C. for about 3–4 hours (depending on the size and shape of the bar), the molded trans-xanthophyll ester concentrate is removed from the molds in solid form, preferably as solid bars. Alternatively, the purified trans-xanthophyll ester concentrate may be ground into a granular state. Both the granular and bar forms of the trans-xanthophyll ester concentrates are useful for processing into human nutritional supplements in the form of tablets or capsules or for use as food colors.

The final purified trans-xanthophyll ester concentrates obtained by the methods of the present invention contain xanthophyll ester in an amount greater than 40 wt. %, preferably greater than about 55 wt %, and often greater than 70 wt. % measured by spectrophotometry (as per Davies, "Carotenoids," in *Chemistry and Biochemistry of Plant Pigments* edited by Goodwin, Academic Press, London, 1976) in hexane at the wavelength of maximum absorption (around 445 nm for lutein ester using the 1% extinction coefficient $\epsilon$ of 1394 and around 450 nm for zeaxanthin ester using the 1% extinction coefficient $\epsilon$ of 1260), with a substantial absence of pesticide residues even at parts per billion detection levels determined by EPA method SW-846 8080A, and a trans:cis-xanthophyll isomer ratio of at least 9:1 as measured by HPLC peak heights. All of this is a substantial improvement over commercially available lutein ester concentrates, which often contain only as much as 25 wt. % xanthophyll esters, with a trans:cis-isomer ratio of about 75:25. The increased ester content, the increased trans:cis-isomer ratio, and the resultant solid form of the trans-xanthophyll ester concentrates of the present invention make them desirable over prior art concentrates for processing and use in human nutritional supplements in the form of tablets, capsules, or liquid preparations.

The methods of the present invention thus provide desirable alternatives to methods known in the art for producing xanthophyll concentrates. The methods of the present invention are comparatively simple and result directly in concentrates that contain xanthophylls in their natural ester form and also have the desired characteristics of enhanced purity, high xanthophyll ester concentrations, and high trans:cis-xanthophyll isomer ratios. The extracts obtained by the methods of the present invention are thus ideal for use in human nutritional supplements for applications such as treatment of cancer and age-related macular degeneration of the eye.

The invention is now described with reference to the following non-limiting examples. These examples are provided for the purpose of illustration only, and the invention should in no way be construed as being limited to these examples, but rather should be construed to encompass any and all variations which become evident as a result of the teaching provided herein.

EXAMPLE 1

One kilo of dried marigold corollas, having a lutein ester content of 2.9 wt % as determined on an aliquot by Soxhlet extraction and subsequent spectrophotometric measurement at 445 nm which was the wavelength of maximum optical absorption, were percolated with 8 liters of hexane in a glass column fitted with a ceramic filter. The hexane of the resulting solution was evaporated at 60° C. under vacuum. 100 g of oleoresin having a lutein ester content of 27.9% and a 75:25 trans:cis lutein isomer ratio, as determined by HPLC peak heights, were obtained. The oleroresin was stirred for 3 hours with 200 g. isopropanol at 20° C. The resulting suspension was filtered through filter paper, desolventized under vacuum at ambient temperature, melted at 65° C. and poured into molds. After 3 hours of spontaneous cooling to ambient termperature, two lutein ester bars weighing 10 g each and having a lutein ester content of 69.0 wt. % (by spectrophotometry in hexane) and a trans:cis-lutein isomer ratio (by HPLC peak heights) of 90:0 were obtained.

COMPARATIVE EXAMPLE 1

This example, which is included for comparative purposes only, illustrates the process described in Philip, U.S. Pat. No. 4,048,203 for the purification of lutein-fatty acid esters.

Marigold corollas (one kilo) as used in Example 1 were extracted with petroleum ether (3 liters) at room temperature. The extract was evaporated to dryness under vacuum at 50° C. (yield, 100 g). An aliquot of 65 g of the oleoresin was dissolved in hot isopropanol (300 ml) at 75° C.; the solution was filtered through a sintered glass funnel; and the filtrate was cooled to 15° C. The precipitated lutein-fatty acid esters were recovered by filtration and dried under vacuum at 30° C., yielding 23.4 g of concentrate. The lutein ester content was 54 wt % (by spectrophotometry). The isomeric composition of the lutein-fatty acid ester was 70 wt % trans-lutein ester and 30 wt % cis-lutein ester (by HPLC).

The low predominance of the trans-isomer (2.3 fold) of this xanthophyll concentrate and its high cis-isomer content are believed to be the result of the isopropanol treatment being carried out at the high temperature of 75° C. Thus, the xanthophyll concentrate made by this method does not meet the condition of high trans-isomer predominance required for optimum performance as a nutritional supplement.

EXAMPLE 2

This example, in conjunction with Comparative Example 2, demonstrates the enhanced purity, in terms of pesticide content, of lutein ester concentrates obtained from marigold corollas according to the methods of the present invention, as compared to lutein ester concentrates obtained from full marigold flowers according to commonly used procedures.

One kilo of marigold flowers from a normal harvest having a lutein ester content of 1.67 wt %, as determined on an aliquot by Soxhlet extraction with petroleum ether and subsequent spectrophotometric measurement at 445 nm, using $\epsilon^{1\%}=1394$, was separated by hand into corollas and non-corolla flower parts. 500 g of corollas, which contained 3.34 wt % of lutein ester, were extracted by the method used in Example 1, which yielded 48.6 g of oleoresin with a lutein ester content of 33.0 wt % by spectrophotometry. This oleoresin was stirred for 3 hours with 150 ml isopropyl alcohol at ambient temperature (19° C.). The suspension was filtered through filter cloth, and the solid was desolventized under vacuum at ambient temperature. The resulting solid (26.6 grams) contained 41.0 wt % lutein esters, determined by spectrophotometry, with no detectable traces of pesticide residues by EPA method SW-846 8080A (limit of detection: 48 micrograms/kilogram). The lutein ester concentrate was melted at 60° C., poured into molds, and allowed to cool into solid bars for 4 hours to ambient termperature (20° C.).

COMPARATIVE EXAMPLE 2

One kilo of marigold flowers from the same harvest used in Example 2 was extracted by the method used in Example 1, and yielded 88.8 g crude oleoresin with xanthophyll ester content of 16.9 wt %. The crude oleoresin was stirred for 3 hours with 200 ml isopropyl alcohol at ambient temperature (19° C.), filtered, and dried as described in Example 2. A resulting solid (23.0 g) was obtained with a xanthophyll ester content of 40.5 wt %. Pesticide residue analysis of the oleoresin using EPA method SW-846 8080A showed the presence of 0.9 ppm of the pesticide endosulfan.

EXAMPLE 3

Another batch of marigold flowers was extracted and the oleoresin processed as in Example 2. The resulting solid (19.4 grams) contained 56.1 wt % lutein esters.

COMPARATIVE EXAMPLE 3

Another batch of marigold flowers was extracted and the oleoresin processed as in Comparative Example 2. The resulting solid (16.7 grams) contained 55.6 wt % lutein esters. Pesticide residue analysis of the solid using EPS method SW-846 8080A showed the presence of 0.9 ppm of the pesticide endosulfan.

EXAMPLE 4

5 kg dry Chinese wolfberries (*Lycium chinense*) were pre-extracted in a glass column fitted with a ceramic filter by percolation with 90 liters of hot water (80° C.) during 2 hours to eliminate water-soluble gums. The wolfberries were then dehydrated in a fluid-bed dryer at 60° C., milled using a hammer-mill, and slowly (during 8 hours) extracted by percolation at ambient temperature (21° C.) with 40 liters of hexane in a glass column fitted with a ceramic filter. The extract was desolventized under vacuum at 60° C. The resulting solvent-free oleoresin weighed 58 g and contained 11.5 wt % zeaxanthin ester by spectrophotometry of an aliquot dissolved in hexane as described above. This oleoresin was mixed with 250 ml of isopropyl alcohol and stirred for 5 hours at 19° C. Insoluble solids were separated by filtration and desolventized in a rotary vacuum evaporator at 25° C. for 3 hours, yielding 11.9 g. of zeaxanthin ester concentrate, with a zeaxanthin ester content of 56.0 wt %

(determined by spectrophotometry as above) and a trans:cis-zeaxanthin isomer ratio of 9:1 (determined by HPLC peak heights).

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A method of obtaining a trans-xanthophyll ester concentrate of high purity comprising:
   (a) contacting plant material containing xanthophyll esters with a hydrocarbon solvent for a time sufficient to extract xanthophyll esters from the plant material;
   (b) separating the hydrocarbon solvent and extract dissolved therein from the remaining plant material;
   (c) evaporating the hydrocarbon solvent from the dissolved extract to obtain a crude xanthophyll ester concentrate;
   (d) admixing the crude xanthophyll ester concentrate with an alcohol at approximately ambient temperature to dissolve non-xanthophyll impurities and cis-xanthophyll esters from the concentrate; and
   (e) removing the alcohol containing impurities and cis-xanthophyll esters from the crude trans-xanthophyll concentrate to obtain a purified trans-xanthophyll ester concentrate.

2. The method of claim 1, wherein the plant material is selected from the group consisting of marigold flowers, berries of the genus Lycium, and berries of the genus Physalis.

3. The method of claim 1, wherein the hydrocarbon solvent is selected from the group consisting of pentane, hexane, heptane, and mixtures thereof.

4. The method of claim 1, wherein the alcohol is a lower aliphatic alcohol.

5. The method of claim 1, wherein the ambient temperature for admixing with alcohol is maintained between about 18° C. and about 22° C.

6. The method of claim 1, further comprising the steps of melting the purified trans-xanthophyll ester concentrate into molds, cooling the molded trans-xanthophyll ester concentrate, and removing the cooled concentrate from the molds as solid bars.

7. The method of claim 1, further comprising grinding the purified trans-xanthophyll ester concentrate into a granular state.

8. A method of obtaining a trans-lutein ester concentrate of high purity comprising:
   (a) removing all non-corolla flower parts from marigold flowers;
   (b) contacting the marigold corollas with a hydrocarbon solvent for a time sufficient to extract lutein esters from the corollas;
   (c) separating the hydrocarbon solvent and extract dissolved therein from the remaining corollas;
   (d) evaporating the hydrocarbon solvent from the dissolved extract to obtain a crude lutein ester concentrate;
   (e) admixing the crude lutein ester concentrate with an alcohol at approximately ambient temperature to dissolve non-xanthophyll impurities and cis-lutein esters from the concentrate; and
   (f) removing the alcohol containing impurities and cis-lutein esters from the crude trans-lutein concentrate to obtain a purified trans-lutein ester concentrate.

9. The method of claim 8, wherein the hydrocarbon solvent is selected from the group consisting of pentane, hexane, heptane, and mixtures thereof.

10. The method of claim 8, wherein the alcohol is a lower aliphatic alcohol.

11. The method of claim 8, wherein the ambient temperature for admixing with alcohol is maintained between about 18° C. and about 22° C.

12. A trans-xanthophyll ester concentrate wherein the trans-xanthophyll ester content of the concentrate is at least four times greater than the cis-xanthophyll ester content of the concentrate.

13. The trans-xanthophyll ester concentrate according to claim 12, wherein the total concentration of trans- and cis-xanthophyll esters is at least about 40% by weight of the concentrate.

14. The trans-xanthophyll ester concentrate according to claim 12, wherein pesticide residues are substantially absent from the concentrate at parts per billion detection levels.

15. The trans-xanthophyll ester concentrate according to claim 12, wherein the xanthophyll of the ester comprises at least substantially lutein.

16. The trans-xanthophyll ester concentrate according to claim 12, wherein the xanthophyll of the ester comprises at least substantially zeaxanthin.

17. A dietary supplement for human nutrition comprising a trans-xanthophyll ester concentrate according to claim 12.

18. A trans-xanthophyll ester concentrate wherein the xanthophyll ester content is greater than about 55% by weight of the concentrate.

19. The trans-xanthophyll ester concentrate according to claim 18, wherein the trans-xanthophyll ester content of the concentrate is at least four times greater than the cis-xanthophyll ester content of the concentrate.

20. The trans-xanthophyll ester concentrate according to claim 17, wherein pesticide residues are substantially absent from the concentrate at parts per billion detection levels.

21. The trans-xanthophyll ester concentrate according to claim 18, wherein the xanthophyll of the ester comprises at least substantially lutein.

22. The trans-xanthophyll ester concentrate according to claim 18, wherein the xanthophyll of the ester comprises at least substantially zeaxanthin.

23. A dietary supplement for human nutrition comprising a trans-xanthophyll concentrate according to claim 18.

* * * * *

UNITED STATES PATENT AND TRADEMARK OFFICE
CERTIFICATE OF CORRECTION

PATENT NO. : 6,191,293 B1
DATED : February 20, 2001
INVENTOR(S) : Luis W. Levy

It is certified that error appears in the above-identified patent and that said Letters Patent is hereby corrected as shown below:

<u>Column 7,</u>
Line 34, "90:0" should read -- 90:10 --

Signed and Sealed this

Second Day of October, 2001

*Attest:*

NICHOLAS P. GODICI
*Attesting Officer*     *Acting Director of the United States Patent and Trademark Office*